(12) United States Patent
Chodkowski

(10) Patent No.: US 10,188,819 B2
(45) Date of Patent: Jan. 29, 2019

(54) MOTION STABILIZER SYSTEM FOR RESPIRATORY INTERFACE DEVICE

(71) Applicant: KONINKLIJKE PHILIPS N.V., Eindhoven (NL)

(72) Inventor: Lauren Patricia Chodkowski, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 715 days.

(21) Appl. No.: 14/652,798

(22) PCT Filed: Dec. 12, 2013

(86) PCT No.: PCT/IB2013/060858
§ 371 (c)(1),
(2) Date: Jun. 17, 2015

(87) PCT Pub. No.: WO2014/097067
PCT Pub. Date: Jun. 26, 2014

(65) Prior Publication Data
US 2015/0328422 A1   Nov. 19, 2015

Related U.S. Application Data

(60) Provisional application No. 61/738,673, filed on Dec. 18, 2012.

(51) Int. Cl.
*A61M 16/06* (2006.01)
*A61M 16/08* (2006.01)

(52) U.S. Cl.
CPC ........ *A61M 16/0616* (2014.02); *A61M 16/06* (2013.01); *A61M 16/0605* (2014.02); *A61M 16/0683* (2013.01); *A61M 16/08* (2013.01)

(58) Field of Classification Search
CPC .............. A61M 16/06; A61M 16/0605; A61M 16/0611; A61M 16/0616; A61M 16/0622; A61M 16/0627; A61M 16/0633; A61M 16/0644; A61M 16/0683; A61M 2016/0661; A61M 16/0666; A61M 16/08; A61M 16/0816; A61M 16/0825;
(Continued)

(56) References Cited

U.S. PATENT DOCUMENTS 4,817,926 A * 4/1989 Schwerdt ............ F16F 13/1463
267/140.12
4,867,154 A * 9/1989 Potter ................ A61M 16/0488
128/207.17
(Continued)

FOREIGN PATENT DOCUMENTS

WO   WO2011110968 A2   9/2011
WO   WO2012020359 A1   2/2012
WO   WO2012069951 A1   5/2012

*Primary Examiner* — (Jackie) Tan-Uyen T Ho
*Assistant Examiner* — Joseph D Boecker
(74) *Attorney, Agent, or Firm* — Michael W. Haas

(57) ABSTRACT

A floatable coupling between a patient interface device and a frame body is provided. The floatable coupling includes a number of elastic bands extending between the patient interface device and the frame body. The elastic bands couple the patient interface device and the frame body in a manner that allows the patient interface device to float relative to the frame body.

20 Claims, 5 Drawing Sheets

(58) Field of Classification Search
CPC ....... A62B 18/00; A62B 18/02; A62B 18/025; A62B 18/06; A62B 18/084; A41D 13/11
USPC ............ 128/206.21, 206.24, 206.27, 206.28, 128/207.13, 207.17, 207.18; 403/225–228; 267/140.12
See application file for complete search history.

(56) References Cited

U.S. PATENT DOCUMENTS

| | | | | |
|---|---|---|---|---|
| 4,871,152 | A * | 10/1989 | Funahashi | F16F 13/14 267/140.12 |
| 5,121,745 | A | 6/1992 | Israel | |
| 5,553,834 | A * | 9/1996 | Je | F16C 27/04 188/307 |
| 6,595,214 | B1 * | 7/2003 | Hecker | A61M 16/06 128/206.21 |
| 7,546,837 | B2 | 6/2009 | Busch | |
| 7,866,639 | B2 * | 1/2011 | Endo | F16F 13/14 267/140.12 |
| 8,146,595 | B2 * | 4/2012 | Sherman | A61M 16/06 128/206.21 |
| 8,967,598 | B2 * | 3/2015 | Whear | F16F 3/0873 267/140.12 |
| 2002/0029780 | A1 * | 3/2002 | Frater | A61M 16/06 128/206.24 |
| 2003/0196656 | A1 | 10/2003 | Moore | |
| 2006/0231101 | A1 * | 10/2006 | Cannon | A61M 16/0488 128/206.29 |
| 2006/0272646 | A1 * | 12/2006 | Ho | A61M 16/0683 128/207.11 |
| 2007/0044804 | A1 * | 3/2007 | Matula, Jr. | A61M 16/06 128/206.21 |
| 2007/0111374 | A1 | 5/2007 | Islam | |
| 2009/0014008 | A1 * | 1/2009 | Takishita | A61M 16/06 128/207.11 |
| 2009/0176051 | A1 | 7/2009 | Eifler | |
| 2009/0223521 | A1 * | 9/2009 | Howard | A61M 16/06 128/206.23 |
| 2011/0226255 | A1 | 9/2011 | Rothermel | |
| 2012/0152255 | A1 * | 6/2012 | Barlow | A61M 16/0066 128/205.25 |
| 2012/0305001 | A1 * | 12/2012 | Tatkov | A61M 16/06 128/205.25 |
| 2013/0199537 | A1 * | 8/2013 | Formica | A61M 16/06 128/205.25 |
| 2014/0338671 | A1 * | 11/2014 | Chodkowski | A61M 16/06 128/205.25 |
| 2015/0047640 | A1 * | 2/2015 | Mccaslin | A61M 16/06 128/205.25 |
| 2015/0283349 | A1 * | 10/2015 | McLaren | A61M 16/06 128/206.21 |
| 2015/0328423 | A1 * | 11/2015 | Siew | A61M 16/06 128/205.25 |
| 2016/0136375 | A1 * | 5/2016 | Zhan | A61M 16/0644 128/205.25 |
| 2017/0368286 | A1 * | 12/2017 | Grashow | A61M 16/0611 |

* cited by examiner

MOTION STABILIZER SYSTEM FOR RESPIRATORY INTERFACE DEVICE

CROSS-REFERENCE TO RELATED APPLICATIONS

This patent application claims the priority benefit under 35 U.S.C. of international patent application no. PCT/IB2013/060858, filed Dec. 12, 2013, which claims the priority benefit under 35 U.S.C. § 119(e) of U.S. Provisional Application No. 61/738,673, filed on Dec. 18, 2012, the contents of which are herein incorporated by reference.

BACKGROUND OF THE INVENTION

1. Field of the Invention

The present invention relates to respiratory interface devices for transporting a gas to and/or from an airway of a user which include, but are not limited to, a patient interface device and a support assembly and, in particular, to a respiratory interface devices wherein the patient interface device is floatably coupled to a support assembly.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to split open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device such as, but not limited to, a mask component having a soft, flexible sealing cushion on the face of a patient. The respiratory interface device component may be, without limitation, a nasal mask that covers the patient's nose, a nasal/oral mask that covers the patient's nose and mouth, or a full face mask that covers the patient's face. While any type patient interface device may be used, the following description shall use a nasal mask as an example. Such patient interface devices may also employ other patient contacting components, such as a support assembly including a frame with forehead supports, cheek pads or chin pads. The patient interface device is connected to a gas delivery tube or conduit and interfaces the ventilator or pressure support device with the airway of the patient, so that a flow of breathing gas can be delivered from the pressure/flow generating device to the airway of the patient.

One requisite of many of these respiratory interface devices, particularly medical respiratory interface devices, is that they provide an effective fit against the user's face and that the respiratory interface device contours with the user's face to limit or prevent leakage of the gas being supplied. The fit of a respiratory interface device is partially controlled by the interaction between the patient interface device and the support assembly. That is, a support assembly may include a rigid frame and a number of support members, such as, but not limited to, straps. The patient interface device is coupled to the frame. The support members are coupled to the frame and extend about the user's head.

This configuration positions the patient interface device to cover the user's nose and provides an effective fit against the user's face. This fit, however, may be effected when the user moves during sleep. That is, for example, a user may roll their head to the side while asleep. When the frame contacts a pillow or mattress, the frame may shift relative to the user's face and disturb the fit of the patient interface device. More specifically, the patient interface device is coupled to the frame in such a manner that the patient interface device moves with the frame. Thus, when the frame shifts relative to the user's face, the patient interface device shifts relative to the user's face.

One improvement to this configuration incorporated a flexible coupling, such as, but not limited to, a multi-pleated bellows, between the frame and the patient interface device cushion. That is, the patient interface device includes a cushion that engages the user's face and creates a seal. The flexible couplings allowed the cushion to remain substantially in the same position relative to the user's face even if the frame were to shift relative to the user's face. The disadvantage was that the flexible couplings occupied a space about the same size as the cushion. In this configuration, the frame that accommodated both the cushion and the flexible couplings could be found to be uncomfortable and unwieldy. Further, the flexible couplings, along with the rest of the patient interface device, needed to be cleaned and the folds of the flexible couplings made cleaning difficult.

SUMMARY OF THE INVENTION

Accordingly, it is an object of the present invention to provide a floatable coupling between the patient interface device and the frame that overcomes the shortcomings of conventional sealing cushions. This object is achieved according to one embodiment of the present invention by providing an elastic coupling assembly including a number of elastic bands. The elastic bands couple the patient interface device and the frame in a manner that allows the patient interface device to float relative to the frame.

In one embodiment, a respiratory interface device includes a patient interface device, a support assembly, and an elastic coupling assembly. The patient interface device includes a body, the patient interface device body including an outer side. The support assembly includes a frame body, the frame body defining an opening. When the patient interface assembly is in use, the frame body opening is generally disposed in front of a user's nose. The patient interface device body outer side is disposed adjacent the frame body opening. The elastic coupling assembly includes a number of elastic bands, each elastic band including a first end and a second end. Each elastic band first end is coupled to the frame body adjacent the frame body opening. Each elastic band second end is coupled to the patient interface device body outer side. In this configuration, the patient interface device body is floatably coupled to the frame body.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the

DETAILED DESCRIPTION OF EXEMPLARY EMBODIMENTS

Figure 1:
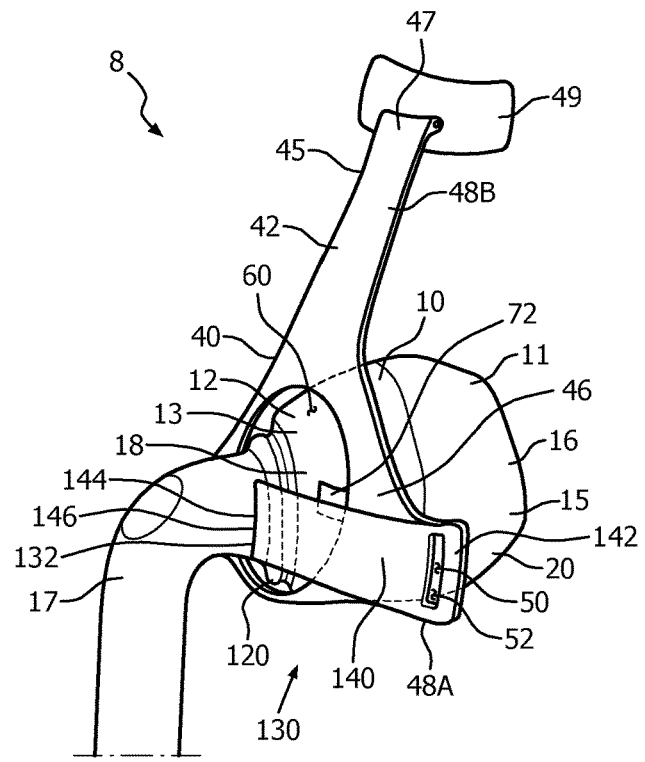
FIG. 1 is an isometric view of a respiratory interface device.

As used herein, the singular form of "a," "an," and "the" include plural references unless the context clearly dictates otherwise. As used herein, the term "number" shall mean one or an integer greater than one (i.e., a plurality).

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, "floatably coupled" means that two elements are coupled to each other but may also move within a limited range relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. As used herein, "a generally continuous seal" can have a gap or can gap when the user moves. As used herein, "a more complete seal" has a gap that is shorter in length than a gap of a generally continuous seal, or, is resistant to gapping when the user moves.

As used herein, "correspond" indicates that two structural components are sized to engage or contact each other with a minimum amount of friction. Thus, an opening which corresponds to a member is sized slightly larger than the member so that the member can pass through the opening with a minimum amount of friction. This definition is modified if the two components are said to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening.

As used herein, a "coupling" or a "coupling component" is one element of a coupling assembly. That is, a coupling assembly includes at least two elements, or components, that are structured to be coupled together. It is understood that the elements of a coupling assembly correspond to each other or are otherwise structured to be joined together. For example, in a coupling assembly, if one coupling element is a bolt, the other coupling element is a nut. Further, it is understood that the two elements of a coupling assembly may not be described at the same time.

FIG. 1 shows a respiratory interface device 8 according to an exemplary embodiment of the invention. Respiratory interface device 8 includes a patient interface device 10, a support assembly 40, and an elastic coupling assembly 70. Patient interface device 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV)® device, proportional positive airway pressure (PPAP) device, C-Flex™ device, Bi-Flex™ device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

Patient interface device 10 includes a body 11 with a support element 12, such as, but not limited to, a faceplate 13 and a sealing assembly 15 such as, but not limited to, a cushion 16, discussed below. Patient interface device body 11 has an outer side 18 which is the side disposed away from the user's face when patient interface device 10 is in use. In an exemplary embodiment, faceplate 13 is substantially rigid. In an exemplary embodiment, shown in FIG. 1, faceplate 13 is a single piece structured to cover the user's nose. That is, patient interface device 10 has a peripheral contour that is structured to extend over a user's nose. Patient interface device body outer side 18, including faceplate 13, is in an exemplary embodiment, generally convex. In an exemplary embodiment, body 11 is coextensive with faceplate 13. It is understood that this is an exemplary embodiment and patient interface device 10 may be structured to extend over the user's nose and mouth, or, just the user's mouth. Further, it is understood that the faceplate 13 may be made from a soft or flexible material.

Figure 2:
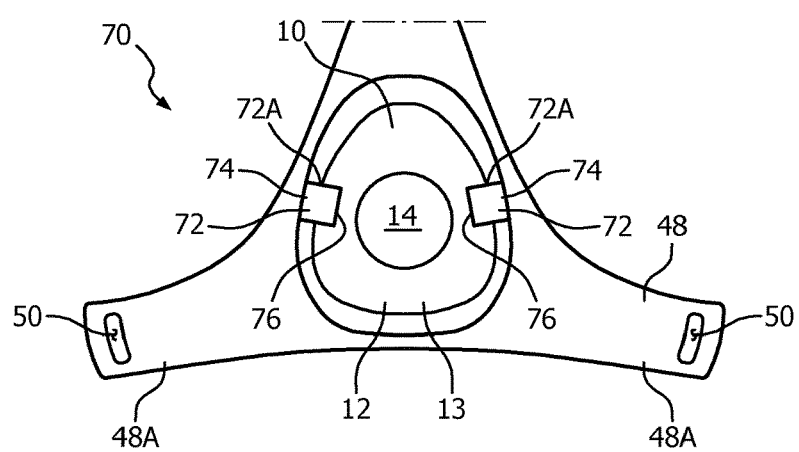
FIG. 2 is a front view of a respiratory interface device with selected elements removed for clarity.

Patient interface device 10, and more specifically faceplate 13, defines an opening 14 (FIG. 2). Patient interface device opening 14 can function as a gas inlet. Patient interface device opening 14 can be coupled to a fluid conduit coupling device 17, as shown in FIG. 1, such as a swivel conduit, for carrying gas such as air between patient interface device 10 and an external gas source (not shown), such as a blower, or any other suitable device. It is contemplated that the external gas source can encompass, without limitation, any gas delivery or gas generation system capable of supplying gas for consumption by a user. Non-limiting examples of various gas delivery therapies can include, but are not limited to, continuous positive airway pressure (CPAP) therapy, auto-titration positive airway pressure therapy, and bi-level positive airway pressure therapy, as noted above. The particular fluid conduit coupling device 17, shown in FIG. 1, is not meant to be limiting and it should be understood that the present invention contemplates a variety of different coupling devices that could be attached, either permanently or selectively, to lower opening 14 to carry gas to or from patient interface device 10. Thus, a variety of coupling devices (e.g., with or without swivels on one or both ends, and with or without an exhalation system formed integral to the device) may be substituted for fluid conduit coupling device 17.

Cushion 16 is structured to extend from faceplate 13 toward the user's face and generally defines the depth of patient interface device 10. That is, cushion 16 defines an interior space. Lower opening 14 is in fluid communication with the interior space defined by cushion 16. Cushion 16 includes a cushion body 20 made from a flexible material. Cushion 16 is structured to engage the user's face and provide a generally continuous seal. This seal may be improved to be a more complete seal if patient interface device 10 is maintained in an orientation that is generally tangent relative to the user's face.

Support assembly 40 includes a frame body 42 and a number of support devices (not shown). In an exemplary embodiment, support devices are straps such as, but not limited to, elastic straps. Frame body 42 includes a central portion 46 and a number of coupling portions 48. In an exemplary embodiment, frame body coupling portions 48 extend from frame body central portion 46 in a number of directions. As shown, a lateral frame body coupling portion 48A extends generally horizontally from frame member central portion 46 and includes a coupling component 50 that may be coupled to a support device (not shown). In an exemplary embodiment, frame body coupling component 50 is a slot 52 through which a strap (not shown) may be looped. It is understood that other types of coupling devices may be used to couple frame body 42 and support devices. Another frame body coupling portion 48B is an elongated connecting member 45 having a distal end 47 that is connected to an adjustable forehead support assembly 49.

Frame body 42, and more specifically frame body central portion 46, defines an opening 60. Frame body 42 is structured so that, when frame body 42 is in use, frame body opening 60 is disposed in front of a user's nose. That is, support assembly 40 is structured so that, when in use, frame body central portion 46, as well as frame body opening 60, is disposed in front of a user's nose. In an exemplary embodiment, frame body opening 60 is generally circular. When patient interface device 10 has a peripheral contour that is structured to extend over a user's nose, frame body opening 60 has a diameter of between about 25 mm and 45 mm, and may be about 35 mm. In this configuration, a portion of faceplate 13 may extend through frame body opening 60 without contacting the surface defining frame body opening 60.

Figure 3:
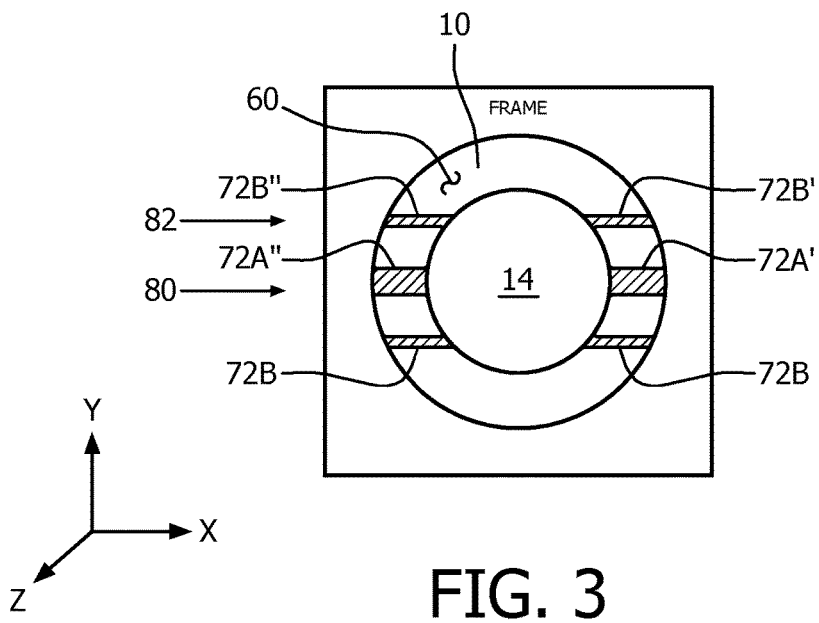
FIG. 3 is a front view of one exemplary embodiment of an elastic coupling assembly.
Figure 4:
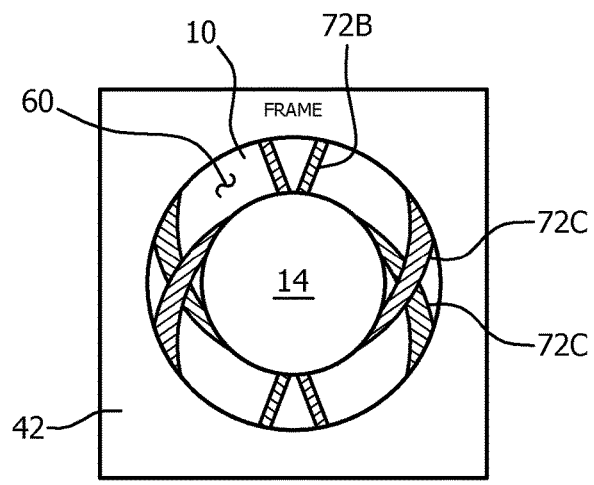
FIG. 4 is a front view of another exemplary embodiment of an elastic coupling assembly.

As shown in FIGS. 1-2, elastic coupling assembly 70 floatably couples patient interface device 10 and support assembly 40. Elastic coupling assembly 70 includes a number of elastic bands 72. Each elastic band includes a first end 74 and a second end 76. In an exemplary embodiment, elastic bands 72 are made from silicone, elastic fabric, or other elastic materials. Each elastic band first end 74 is coupled to frame body 42 at a location adjacent frame body opening 60. Each elastic band second end 76 is coupled to patient interface device body outer side 18. More specifically, patient interface device 10 is positioned with patient interface device opening 14 disposed adjacent frame body opening 60 and each elastic band second end 76 is coupled to patient interface device body outer side 18 adjacent patient interface device opening 14. In an exemplary embodiment, patient interface device opening 14 is generally circular. Thus, as shown in FIGS. 3-4, relative to patient interface device opening 14, elastic bands 72 may be selected from the group including radial elastic bands 72A, secant elastic bands 72B, or tangent elastic bands 72C. That is, as used herein, "radial elastic band" 72A is an elastic band that extends, i.e. has an axis that extends in a direction, generally radially away from the center of patient interface device opening 14.

As used herein, "secant elastic band" 72B is an elastic band that extends at an angle of less than 90 degrees, but more than 0 degrees, relative to the edge of patient interface device opening 14. As used herein, "tangent elastic band" 72C is an elastic band that extends generally tangentially to the edge of patient interface device opening 14. Further, while the terms "radial," "secant," and "tangent" are generally associated with a circular shape, it is understood that patient interface device opening 14 may have any shape and that the nature of the terms, i.e. the association with a circular shape, is not limiting upon the claims. For example, if patient interface device opening 14 were square, a band 72 having an axis extending normal to the edge and aligned with the center of patient interface device opening 14 would be "radial band 72A," whereas band 72 having an axis extending parallel to an adjacent edge of patient interface device opening 14 would be "tangent band 72C."

In an exemplary embodiment, the number of elastic bands 72 includes a number of groups 80, 82 of elastic bands 72 wherein each elastic band 72 in a group of elastic bands includes a similar set of physical characteristics and wherein the different groups of elastic bands 80, 82 include different physical characteristics. As used herein, "physical characteristics" includes, but is not limited to, the dimensions of elastic bands 72 and the material characteristics, e.g. hardness, of elastic bands 72. Thus, for example and as shown in FIG. 3, elastic coupling assembly 70 may include two radial elastic bands 72A and four secant elastic bands 72B. Radial elastic bands 72A are in a first group 80 and each radial elastic band 72A in first group 80 has similar physical characteristics. Conversely, secant elastic bands 72B are in a second group 82 and each radial elastic band 72B in second group 82 has similar physical characteristics with each other, but different physical characteristics than radial elastic bands 72A in first group 80.

More specifically, the number of elastic bands 72 includes a first horizontal radial elastic band 72A' and second horizontal radial elastic band 72A". As shown, first horizontal radial elastic band second end 76 and second horizontal radial elastic band second end 76 are each directly coupled to opposing horizontal sides of patient interface device body opening 14. Further, the number of elastic bands 72 includes a third horizontal secant elastic band 72B' and a fourth horizontal secant elastic band 72B".

A "horizontal" secant elastic band 72B is a secant elastic band 72B that also extends generally horizontally. It is noted that a fifth and sixth horizontal secant elastic bands are also shown. As shown, first horizontal radial elastic band 72A' and second horizontal radial elastic band 72A" have a greater vertical dimension than third horizontal secant elastic band 72B' and a fourth horizontal secant elastic band 72B". Thus, first horizontal radial elastic band 72A' and second horizontal radial elastic band 72A" are in first group 80 of elastic bands 72 having similar physical characteristics, and, third horizontal secant elastic band 72B' and fourth horizontal secant elastic band 72B" are in second group 82 of elastic bands 72 having similar physical characteristics.

In an exemplary embodiment, elastic coupling assembly 70 includes two elastic bands 72. As shown in FIG. 2, two elastic bands 72 may be radial elastic bands 72A that extend generally horizontally. In another exemplary embodiment (not shown), elastic coupling assembly 70 includes two elastic bands 72 which are radial elastic bands 72A that extend generally vertically. Thus, radial elastic bands 72A may be selected from the group including horizontal radial bands or vertical radial bands.

Figure 5:
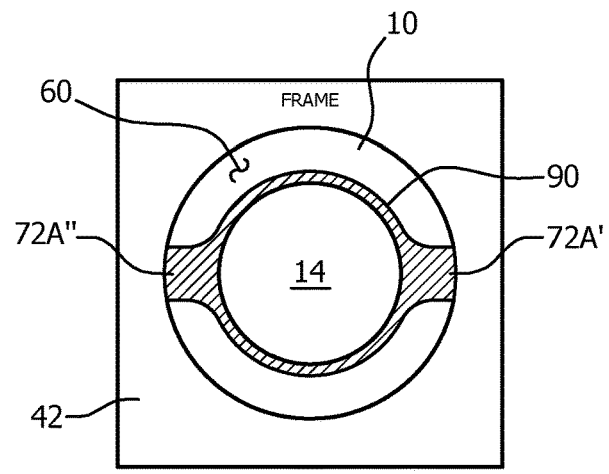
FIG. 5 is a front view of another exemplary embodiment of an elastic coupling assembly.
Figure 6:
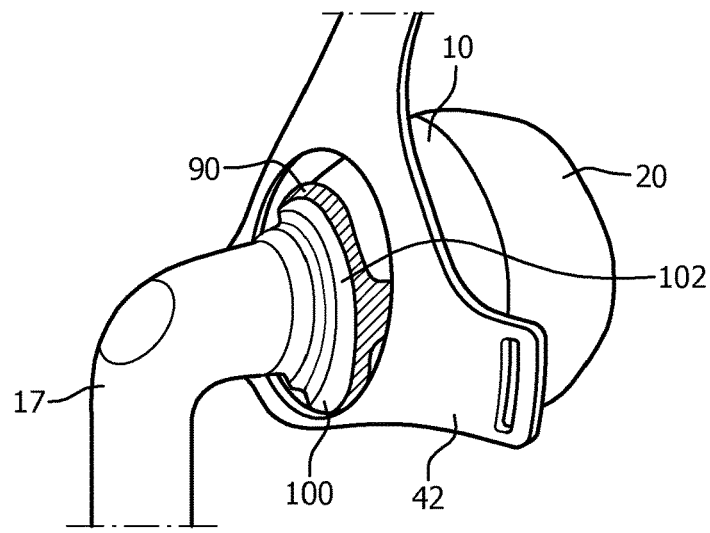
FIG. 6 is an isometric view of the elastic coupling assembly shown in FIG. 5.

As noted above, each elastic band first end 74 is coupled to frame body 42 at a location adjacent frame body opening 60, and, each elastic band second end 76 is coupled to patient interface device body outer side 18. In an exemplary embodiment, as shown in FIG. 2, each elastic band first end 74 is directly coupled to frame body 42 at a location adjacent frame body opening 60, and each elastic band second end 76 is directly coupled to patient interface device body outer side 18. In one exemplary embodiment, shown in FIGS. 5-6, elastic coupling assembly 70 includes an elastic ring 90. Elastic ring 90 is sized to extend about patient interface device opening 14. Elastic ring 90 may be unitary with elastic bands 72.

That is, elastic ring 90 is integral with a number of elastic band first ends 74. To aid in coupling elastic ring 90 to patient interface device body outer side 18, patient interface device body outer side 18 may include a mounting surface 100 disposed about the patient interface device body opening 14. Mounting surface 100 may be a ledge 102 that extends generally normal to patient interface device body outer side 18 about the patient interface device body opening 14. Ledge 102 may have a convex surface so as to trap elastic ring 90 on mounting surface 100. In an embodiment utilizing elastic ring 90, elastic band first ends 74 are, as used herein, coupled to patient interface device body outer side 18 via elastic ring 90 at a location adjacent frame body opening 14.

Figure 7:
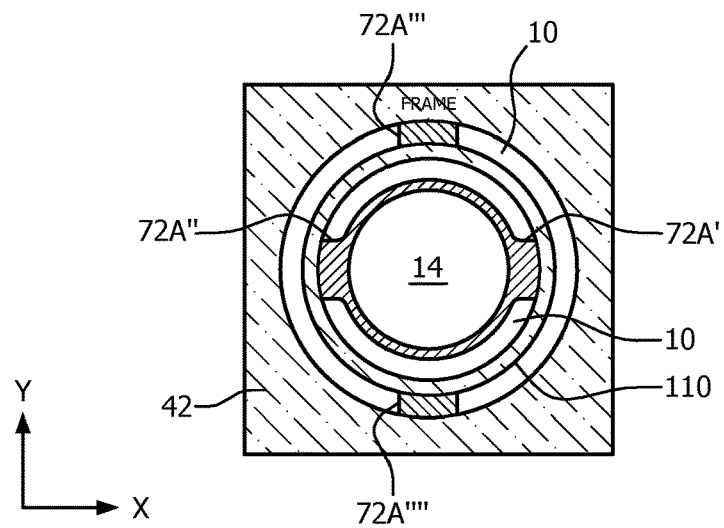
FIG. 7 is a front view of another exemplary embodiment of an elastic coupling assembly.

In another exemplary embodiment, shown in FIG. 7, elastic coupling assembly 70 includes a rigid ring 110. Rigid ring 110 is disposed between frame body opening 60 and patient interface device body outer side 18. Rigid ring 110 provides a coupling location for selected elastic bands 72. For example, as shown, elastic coupling assembly 70 includes a first horizontal radial elastic band 72A' and second horizontal radial elastic band 72A" as well as a first vertical radial elastic band 72A''', and a second vertical radial elastic band 72A''''. First vertical radial elastic band first end 74 and the second vertical radial elastic band first end 74 are each directly coupled to frame body 42 at a location adjacent frame body opening 60. First vertical radial elastic band second end 76 and second vertical radial elastic band second end 76 are directly coupled to opposing vertical portions of rigid ring 110. First horizontal radial elastic band first end 74 and the second horizontal radial elastic band first end 74 are each directly coupled to rigid ring 110.

Figure 8:
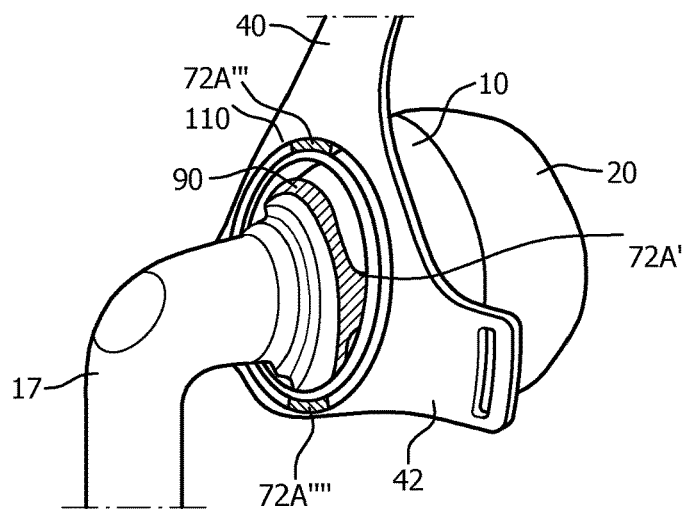
FIG. 8 is an isometric view of another exemplary embodiment of an elastic coupling assembly.
Figure 9A:
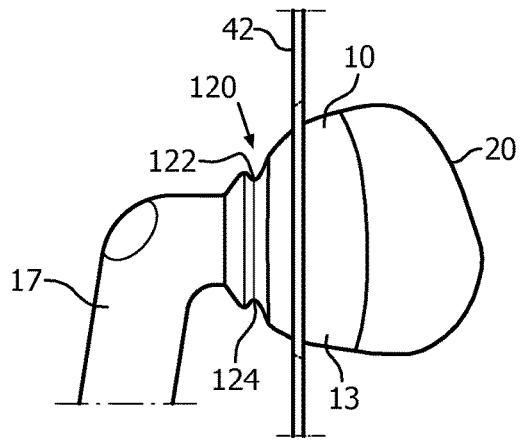
FIG. 9A is a side view of a respiratory interface device with a flexible coupling in a first position.
Figures 9B, 9C:
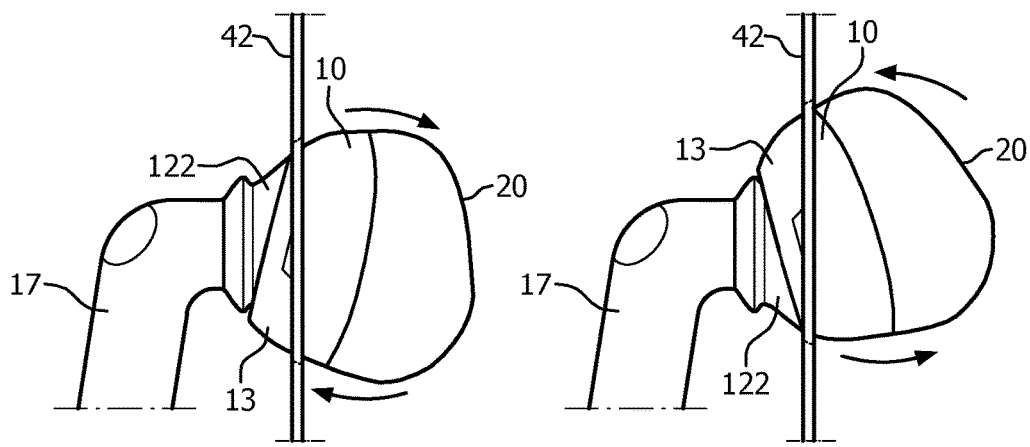
FIG. 9B is a side view of a respiratory interface device with a flexible coupling in a second position.
FIG. 9C is a side view of a respiratory interface device with a flexible coupling in a third position.

First horizontal radial elastic band second end 76 and second horizontal radial elastic band second end 76 are directly coupled to patient interface device body outer side 18. In this configuration, elastic coupling assembly 70 provides patient interface device 10 with two distinct axes of rotation relative to frame body 42. Patient interface device 10 may, however, move perpendicular to the plane defined by the two axes by stretching elastic bands 72 in elastic coupling assembly 70. As shown in FIG. 8, another exemplary embodiment includes both elastic ring 90 and rigid ring 110. This embodiment is substantially similar to the embodiment described immediately above, except that first horizontal radial elastic band 72A' and second horizontal radial elastic band 72A" are unitary with elastic ring 90.

As noted above, patient interface device body opening 14 can function as a gas inlet. More specifically, fluid conduit coupling device 17 is coupled to faceplate 13 (or patient interface device body 11) at patient interface device body opening 14. As the weight of fluid conduit coupling device 17 (and any conduit for transporting gas coupled thereto) may affect the orientation of patient interface device 10, it is desirable to provide a movable coupling at the interface of fluid conduit coupling device 17 and faceplate 13. Further, in an exemplary embodiment, fluid conduit coupling device 17 has a shape similar to patient interface device body opening 14. Thus, in the exemplary embodiment, fluid conduit coupling device 17 and patient interface device body opening 14 have a generally circular shape.

To reduce any force from the weight of fluid conduit coupling device 17 (and any conduit for transporting gas coupled thereto) in patient interface device 10, and as shown in FIGS. 1 and 9A-9C, patient interface device body 11 includes a flexible coupling 120 disposed about patient interface device body opening 14. In an exemplary embodiment, flexible coupling 120 is a bellow(s) 122. "Bellow" 122, as used herein, is a flexible membrane 124 extending between the two elements being coupled. That is, in this exemplary embodiment, flexible membrane 124 extends between, and is coupled to, both patient interface device body 11 and fluid conduit coupling device 17. Further, flexible membrane 124 extends about patient interface device body opening 14. As shown, bellow 122 has a single convex fold or pleat. It is understood that multiple folds or pleats may exist in flexible membrane 124. As show in FIGS. 9A-9C, bellow 122 allows fluid conduit coupling device 17 to remain in a substantially fixed orientation relative to frame body 42 while patient interface device 10 moves relative to frame body 42.

Moreover, it is desirable that fluid conduit coupling device 17 remains in a substantially fixed orientation relative to frame body 42 while patient interface device 10 moves relative to frame body 42. Accordingly, frame body 42 includes a fluid conduit coupling device stabilizer 130, as shown in FIG. 1. Fluid conduit coupling device stabilizer 130 is structured to maintain fluid conduit coupling device 17 in a substantially fixed orientation relative to frame body 42. Accordingly, fluid conduit coupling device stabilizer 130 is fixed to frame body 42 and includes a coupling element 132 that is coupled to fluid conduit coupling device 17. In the exemplary embodiment shown in FIG. 1, fluid conduit coupling device stabilizer 130 includes two rigid, elongated members 140 (one shown, hereinafter, "stabilizer member") disposed on opposite sides of fluid conduit coupling device 17.

Each stabilizer member has a first end 142 and a second end 144. Stabilizer member first end 142 is coupled to frame body 42 in a fixed orientation. Stabilizer member second end 144 includes stabilizer member coupling element 132. In the exemplary embodiment, stabilizer member coupling element 132 is a shaped end 146 structured to correspond to the shape of fluid conduit coupling device 17. Thus, in an embodiment wherein fluid conduit coupling device 17 is generally circular, stabilizer member coupling element 132 is a convex shaped end 146. Two opposed stabilizer member coupling element shaped ends 146 (one shown), trap fluid conduit coupling device 17 in a substantially fixed orientation relative to frame body 42. It is noted that fluid conduit coupling device stabilizer 130 having two opposed elongated members 140 is one exemplary embodiment; fluid conduit coupling device stabilizer 130 may have any shape including, but not limited to, a collar (not shown) extending about fluid conduit coupling device 17 and fixed to frame body 42 by a single elongated member (not shown).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory interface device comprising:
   a patient interface device including a body, the patient interface device body including an outer side;
   a support assembly including a frame body, the frame body defining an opening, wherein, when the patient interface assembly is in use, the frame body opening is generally disposed in front of a user's nose;
   the patient interface device body outer side disposed adjacent the frame body opening; and
   an elastic coupling assembly including a number of elastic bands, each elastic band including a first end and a second end, wherein each elastic band first end is coupled to the frame body adjacent the frame body opening, wherein each elastic band second end is coupled to the patient interface device body outer side, and wherein the patient interface device body is floatably coupled to the frame body.

2. The respiratory interface assembly of claim 1, wherein:
   the patient interface device body outer side includes a generally circular opening, wherein the patient interface device body opening is disposed adjacent the frame body opening; and
   wherein the number of elastic bands are selected from the group including radial bands, secant bands, or tangent bands.

3. The respiratory interface assembly of claim 2, wherein:
   the number of elastic bands includes a plurality of groups of elastic bands, each elastic band in a group of elastic bands including a similar set of physical characteristics; and
   wherein the different groups of elastic bands include different physical characteristics.

4. The respiratory interface assembly of claim 2 wherein the radial bands are selected from the group including horizontal radial bands or vertical radial bands.

5. The respiratory interface assembly of claim 2, wherein:
   the patient interface device includes a fluid conduit coupling device;
   the patient interface device body includes a flexible coupling disposed about the patient interface device body opening and coupled to the patient interface device body and the frame body.

6. The respiratory interface assembly of claim 5, wherein the patient interface device body flexible coupling includes a bellow.

7. The respiratory interface assembly of claim 5, wherein:
   the support assembly includes a fluid conduit coupling device stabilizer, the fluid conduit coupling device stabilizer fixed to the frame body;
   the fluid conduit coupling device stabilizer is structured to be coupled to the fluid conduit coupling device and to maintain the fluid conduit coupling device in a substantially fixed relationship to the frame body;
   the fluid conduit coupling device stabilizer coupled to the fluid conduit coupling device; and
   the fluid conduit coupling device is substantially fixed to the frame body.

8. The respiratory interface assembly of claim 7, wherein:
   the fluid conduit coupling device stabilizer includes rigid, elongated members disposed on opposite sides of the fluid conduit coupling device, each stabilizer member including a first end and a second end;
   each stabilizer member first end fixed to the frame body; and
   each stabilizer member second end coupled to the fluid conduit coupling device.

9. The respiratory interface assembly of claim 7, wherein the number of elastic bands are radial bands.

10. The respiratory interface assembly of claim 7, wherein the number of elastic bands are selected from the group including secant bands and tangent bands.

11. A respiratory interface device comprising:
    a patient interface device including a body, the patient interface device body including an outer side;
    a support assembly including a frame body, the frame body defining an opening, wherein, when the patient interface assembly is in use, the frame body opening is generally disposed in front of a user's nose;
    the patient interface device body outer side disposed adjacent the frame body opening;
    an elastic coupling assembly including a number of elastic bands, each elastic band including a first end and a second end, wherein each elastic band first end is coupled to the frame body adjacent the frame body opening, wherein each elastic band second end is coupled to the patient interface device body outer side, and wherein the patient interface device body is floatably coupled to the frame body;
    the patient interface device body outer side includes a generally circular opening, wherein the patient interface device body opening is disposed adjacent the frame body opening;

wherein the number of elastic bands are selected from the group including radial bands, secant bands, or tangent bands;
the number of elastic bands includes a first horizontal radial elastic band and second horizontal radial elastic band; and
the first horizontal radial elastic band second end and the second horizontal radial elastic band second end directly coupled to opposing horizontal sides of the patient interface device body opening.

12. The respiratory interface assembly of claim 11, wherein:
the elastic coupling assembly includes a third horizontal secant elastic band and a fourth horizontal secant elastic band;
the third horizontal secant elastic band second end and the fourth secant horizontal radial elastic band second end directly coupled to opposing horizontal sides of the patient interface device body opening;
wherein the first horizontal radial elastic band and the second horizontal radial elastic band are in a first group of elastic bands having similar physical characteristics; and
wherein the third horizontal secant elastic band and the fourth horizontal secant elastic band are in a second group of elastic bands having similar physical characteristics.

13. The respiratory interface assembly of claim 11, wherein:
the patient interface device body outer side includes a generally circular mounting surface disposed about the patient interface device body opening;
the elastic coupling assembly includes an elastic ring, wherein the elastic ring is coupled to the patient interface device body mounting surface.

14. A respiratory interface device comprising:
a patient interface device including a body, the patient interface device body including an outer side;
a support assembly including a frame body, the frame body defining an opening, wherein, when the patient interface assembly is in use, the frame body opening is generally disposed in front of a user's nose;
the patient interface device body outer side disposed adjacent the frame body opening;
an elastic coupling assembly including a number of elastic bands, each elastic band including a first end and a second end, wherein each elastic band first end is coupled to the frame body adjacent the frame body opening, wherein each elastic band second end is coupled to the patient interface device body outer side, and wherein the patient interface device body is floatably coupled to the frame body;
the patient interface device body outer side includes a generally circular opening, wherein the patient interface device body opening is disposed adjacent the frame body opening;
wherein the number of elastic bands are selected from the group including radial bands, secant bands, or tangent bands;
the elastic coupling assembly including a rigid ring;
the number of elastic bands includes a first horizontal radial elastic band, a second horizontal radial elastic band, a first vertical radial elastic band, and a second vertical radial elastic band;
the first vertical radial elastic band second end and the second vertical radial elastic band second end directly coupled to opposing vertical portions of the rigid ring;
the first horizontal radial elastic band first end and the second horizontal radial elastic band first end directly coupled to opposing horizontal portions of the rigid ring; and
the first horizontal radial elastic band second end and the second horizontal radial elastic band second end directly coupled to opposing horizontal sides of the patient interface device body opening.

15. The respiratory interface assembly of claim 14, wherein:
the patient interface device body outer side includes a generally circular mounting surface (100) disposed about the patient interface device body opening;
the elastic coupling assembly includes an elastic ring, wherein the elastic ring is coupled to the patient interface device body mounting surface.

16. A respiratory interface device comprising:
a patient interface device including a body, the patient interface device body including an outer side;
a support assembly including a frame body, the frame body defining an opening, wherein, when the patient interface assembly is in use, the frame body opening is generally disposed in front of a user's nose;
the patient interface device body outer side disposed adjacent the frame body opening;
an elastic coupling assembly including a number of elastic bands, each elastic band including a first end and a second end, wherein each elastic band first end is coupled to the frame body adjacent the frame body opening, wherein each elastic band second end is coupled to the patient interface device body outer side, and wherein the patient interface device body is floatably coupled to the frame body;
the patient interface device body outer side includes a generally circular opening, wherein the patient interface device body opening is disposed adjacent the frame body opening;
wherein the number of elastic bands are selected from the group including radial bands, secant bands, or tangent bands;
the patient interface device includes a fluid conduit coupling device;
the patient interface device body includes a flexible coupling disposed about the patient interface device body opening and coupled to the patient interface device body and the frame body;
the fluid conduit coupling device stabilizer includes rigid, elongated members disposed on opposite sides of the fluid conduit coupling device, each stabilizer member including a first end and a second end;
each stabilizer member first end fixed to the frame body;
each stabilizer member second end coupled to the fluid conduit coupling device;
wherein the number of elastic bands includes a first horizontal radial elastic band and second horizontal radial elastic band; and
the first horizontal radial elastic band second end and the second horizontal radial elastic band second end directly coupled to opposing horizontal sides of the patient interface device body opening.

17. A respiratory interface device comprising:
a patient interface device including a body, the patient interface device body including an outer side;
a support assembly including a frame body, the frame body defining an opening, wherein, when the patient interface assembly is in use, the frame body opening is generally disposed in front of a user's nose;

the patient interface device body outer side disposed adjacent the frame body opening;

an elastic coupling assembly including a number of elastic bands, each elastic band including a first end and a second end, wherein each elastic band first end is coupled to the frame body adjacent the frame body opening, wherein each elastic band second end is coupled to the patient interface device body outer side, and wherein the patient interface device body is floatably coupled to the frame body;

the patient interface device body outer side includes a generally circular opening, wherein the patient interface device body opening is disposed adjacent the frame body opening;

wherein the number of elastic bands are selected from the group including radial bands, secant bands, or tangent bands;

the patient interface device includes a fluid conduit coupling device;

the patient interface device body includes a flexible coupling disposed about the patient interface device body opening and coupled to the patient interface device body and the frame body;

wherein the number of elastic bands includes a first horizontal radial elastic band and second horizontal radial elastic band; and the first horizontal radial elastic band second end and the second horizontal radial elastic band second end directly coupled to opposing horizontal sides of the patient interface device body opening.

18. The respiratory interface assembly of claim 17, wherein:

the elastic coupling assembly includes a third horizontal radial elastic band and fourth horizontal radial elastic band;

the third horizontal radial elastic band second end and the fourth horizontal radial elastic band second end directly coupled to opposing horizontal sides of the patient interface device body opening;

the first horizontal radial elastic band and the second horizontal radial elastic band including a first set of dimensional characteristics; and the third horizontal radial elastic band and the fourth horizontal radial elastic band including a second set of dimensional characteristics.

19. The respiratory interface assembly of claim 17, wherein:

the patient interface device body outer side includes a generally circular mounting surface disposed about the patient interface device body opening; and the elastic coupling assembly includes an elastic ring, wherein the elastic ring is coupled to the patient interface device body mounting surface.

20. A respiratory interface device comprising:

a patient interface device including a body, the patient interface device body including an outer side;

a support assembly including a frame body, the frame body defining an opening, wherein, when the patient interface assembly is in use, the frame body opening is generally disposed in front of a user's nose;

the patient interface device body outer side disposed adjacent the frame body opening;

an elastic coupling assembly including a number of elastic bands, each elastic band including a first end and a second end, wherein each elastic band first end is coupled to the frame body adjacent the frame body opening, wherein each elastic band second end is coupled to the patient interface device body outer side, and wherein the patient interface device body is floatably coupled to the frame body;

the patient interface device body outer side includes a generally circular opening, wherein the patient interface device body opening is disposed adjacent the frame body opening;

wherein the number of elastic bands are selected from the group including radial bands, secant bands, or tangent bands;

the patient interface device includes a fluid conduit coupling device;

the patient interface device body includes a flexible coupling disposed about the patient interface device body opening and coupled to the patient interface device body and the frame body;

the elastic coupling assembly includes a rigid ring;

the number of elastic bands includes a first horizontal radial elastic band, a second horizontal radial elastic band, a first vertical radial elastic band, and a second vertical radial elastic band;

the first vertical radial elastic band second end and the second vertical radial elastic band second end directly coupled to opposing vertical portions of the rigid ring;

the first horizontal radial elastic band first end and the second horizontal radial elastic band first end directly coupled to opposing horizontal portions of the rigid ring; and the first horizontal radial elastic band second end and the second horizontal radial elastic band second end directly coupled to opposing horizontal sides of the patient interface device body opening.

* * * * *